United States Patent

Tojkander

[11] Patent Number: 6,156,021
[45] Date of Patent: Dec. 5, 2000

[54] ANATOMICAL INTERNALLY MOLDABLE TAMPON

[75] Inventor: Erja Anita Helena Tojkander, Heinola, Finland

[73] Assignee: The Procter & Gamble Company, Cincinnati, Ohio

[21] Appl. No.: 09/029,467
[22] PCT Filed: Sep. 4, 1996
[86] PCT No.: PCT/FI96/00469
§ 371 Date: Jul. 8, 1998
§ 102(e) Date: Jul. 8, 1998
[87] PCT Pub. No.: WO97/09022
PCT Pub. Date: Mar. 13, 1997

[30] Foreign Application Priority Data

Sep. 5, 1995 [FI] Finland .................................... 954152

[51] Int. Cl.[7] ........................................................ A61F 13/15
[52] U.S. Cl. ................... 604/385.17; 604/358; 604/369; 604/385.01; 604/385.12; 604/385.16; 604/385.19
[58] Field of Search ................................ 604/385, 385.1, 604/358, 369, 385.01, 385.12, 385.16, 385.17, 385.19

[56] References Cited

U.S. PATENT DOCUMENTS 3,762,413  10/1973  Hanke ...................................... 128/285

FOREIGN PATENT DOCUMENTS 2064326  12/1979  European Pat. Off. ............... 128/285

Primary Examiner—John G. Weiss
Assistant Examiner—Miley C. Peppers, III
Attorney, Agent, or Firm—Matthew P. Fitzpatrick

[57] ABSTRACT

The invention concerns a tampon (3), which can be inserted into the vagina, or other cavity, and which contains a molding cord (1) the pulling of which causes the tampon to increase its diameter and fill the cavity's inside diameter tightly.

5 Claims, 2 Drawing Sheets

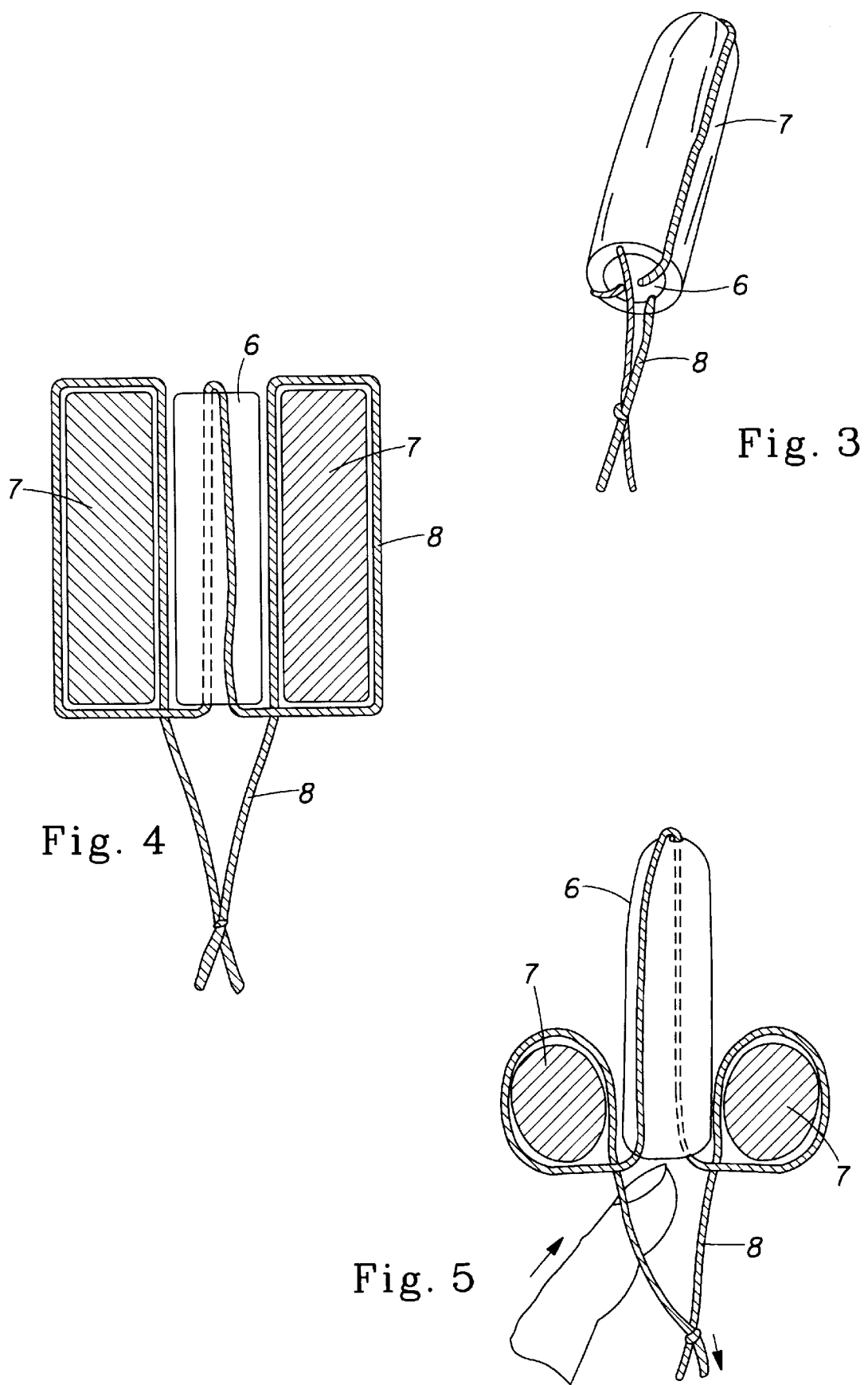

ANATOMICAL INTERNALLY MOLDABLE TAMPON

This invention concerns an anatomical, internally moldable tampon, which may be a tampon intended for the absorption of menstrual flow, or an absorbent tampon intended for some other, for example, medical use.

The tampons used are generally made of highly absorbent materials, such as sterilized cotton fiber, or other highly absorbent fibers. In medical use, tampons are mainly used for the post-operative or post-curettage absorption of blood and body fluids. However, tampons are most commonly used for the absorption of normal menstrual discharge, in other words, as sanitary protection.

The use of tampons as internal sanitary protection is discreet and hygienic, but because of the shape of the vagina and, dependent on the success of the insertion, leakage flows present a problem.

The human vagina is a tubular cavity, normally flattened by tissues, where the center part of the vagina is subject to more pressure than its sides because of the strong muscles in the front and back walls of the vagina. Especially with young and physically active women, these muscles may be comparably strongly developed. For this reason, a tampon often settles along either side of the vagina, thus leaving a channel through which the escaping blood can leak. If a tampon has been incorrectly inserted, it cannot absorb escaping fluids efficiently. Re-insertion of a tampon, which at the initial insertion stage has slipped into an incorrect position, is almost impossible without damaging the tampon.

Several attempts have been made to solve the above mentioned problem. Amongst them one could mention U.S. Pat. Nos. 3,706,311 and 3,762,413. In the former, the essentially bar-like sanitary protection is placed inside a separate applicator folded in half, in which position it is inserted, with the intention that, as it partially unfolds, it will fill the vagina better than if it were straight.

The latter works on the same principle, except that cords have, additionally, been attached to both ends of the oblong tampon, and by pulling the cords this tampon can be made to partially unfold more reliably than the tampon in the first mentioned publication.

Both publications of the state of the art are attempts to improve the situation, but they do not, however, solve the problems connected with a tampon's leak-proof reliability. Neither publication is in any way concerned with the diameter of the tampon, but the manipulation is merely directed to the changing of the shape of a relatively stiff tampon bar. This way, it is impossible to achieve a situation where the vaginal cavity would be well sealed against the flow. In addition, insertion of tampons of the types described above demands great precision.

The basic principle of this invention is to eliminate the above described, and other, drawbacks in this field, and produce a tampon which seals the vaginal cavity extremely well against the flow and which eliminates the problems associated with the need for precision in the insertion, because the tampon can be post-molded inside the vagina, or other cavity, to conform better with the inner contours of the vagina/cavity.

The above mentioned, and other advantages and benefits of the invention, have been achieved with a tampon in the manner characterized in the accompanying claims. In short, a tampon according to the invention is fitted with a molding cord, which can be pulled to increase the tampon's diameter when the tampon is already in the vagina, or other cavity, so that it seals the vagina, or other cavity, better, thus preventing leakage. The tampon's moldability inside the vagina is important, because the diameter of a tampon must be minimized to facilitate its insertion into the vagina but, once in place, the tampon should fill the inner vaginal diameter as closely as possible.

In what follows, the invention is described in greater detail by reference to the accompanying drawings, in which FIG. 1 shows the tampon pushed out of its applicator;

FIG. 3 is a projection of another embodiment of the invention of a tampon which can be inserted with fingers;

FIG. 4 is a longitudinal section of the tampon in FIG. 3

FIG. 5 shows the molding of the tampon shown in FIGS. 3 and 4 by pulling the cord;

Although the following describes the invention only in the context of a tampon for the absorption of menstrual flow, it is understood that the same principles would also apply for other usages. It is equally understood, that presenting the invention by way of the embodiments shown in the accompanying figures in no way limits the invention to these embodiments only.

The figures show two different embodiments of a tampon according to the invention. The first shown embodiment is especially suited for employment with an applicator and the latter can be successfully employed even without an applicator. The same principle applies in both, although the tampons are structurally different.

Figure 1:
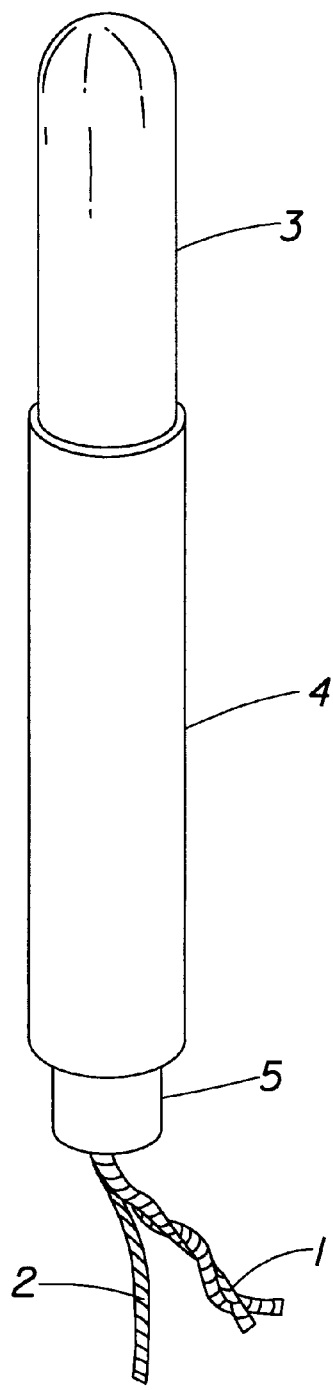
Figure 2:
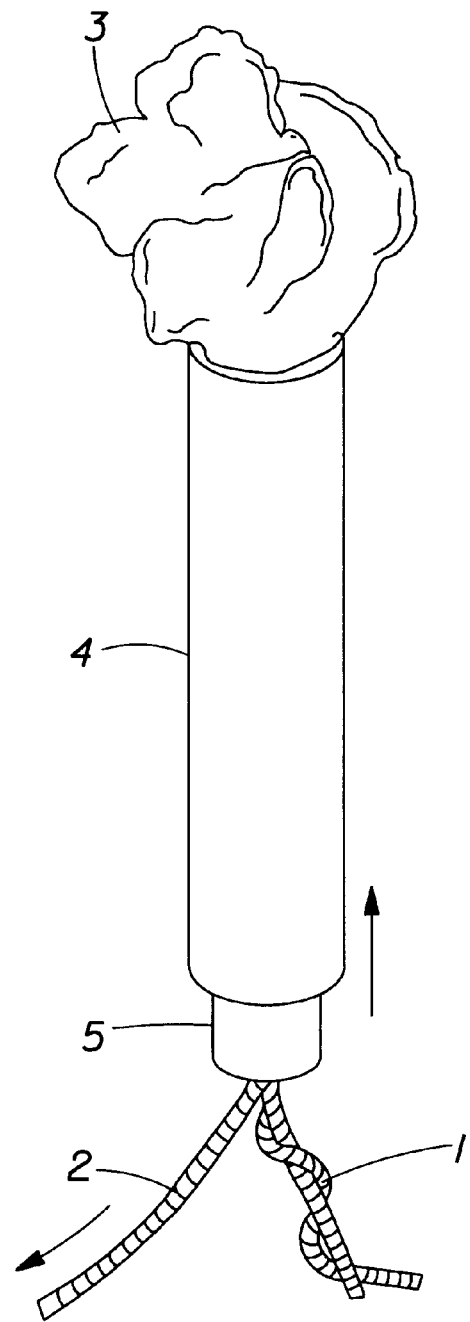
FIG. 2 shows the tampon in FIG. 1, after it has been molded with the pull cord.

FIGS. 1 and 2 show the mode of operation for a tampon with an applicator. At the initial stage the tampon 3 is located inside the applicator tube 4, while the applicator's pushing tube 5 is pulled out as an extension of the applicator tube 4. When the applicator with its tampon has been inserted in the vagina, the tampon is pushed out of the applicator tube 4 with the pushing tube 5. At the same time applicator tube 4 can be pulled out, so that the tampon 3 remains in place.

FIG. 2 shows how the shape of the tampon can be changed inside the vagina by pulling the molding cord 2, attached to the tip of the tampon 3 and threaded inside the tampon's removal cord 1, which is attached by, for example, sewing or otherwise, along the length of the oblong tampon 3, while the tampon is in the vagina, so that the tampon gets compressed against the end of the applicator tube 4, and increases in diameter. Thus, it fills the inside diameter of the vaginal cavity completely. The applicator is removed, and the cords 1 and 2 are left in place. When removing the tampon, the removal cord 1 is pulled, whence the molding cord 2 can slide inside the removal cord, and as the tampon is pulled out subject to slight pressure from the vaginal walls, it regains its elongated shape, making the removal easier.

FIGS. 3, 4 and 5 show, as one embodiment of the invention, the structure of a tampon especially intended for use without an applicator. The tampon's intra-vaginal molding is also done by pulling the removal cord 8 and pressing against the finger 9 in the following manner: the tampon consists of the core layer 6, and the outer layer 7, which is made of relatively loosely compacted material and essentially encloses the layer 6.

After the tampon has been inserted into the vagina, the inserter supports the end of the tampon 6,7 and, at the same time, pulls the cord 8, when the outer leakage protection layer 7 of the layered tampon slides along the core layer 6 to its end, thereby increasing the tampon's overall diameter by the overall diameter of the core layer 6. Again, a very leak-proof sealing of the vaginal cavity is achieved, due to the much increased diameter of the tampon.

The design of the outer layer of the tampon which can be inserted with fingers is simple, and can be realized by forming the removal cord into loops which run first through the core tampon and then run as a loop along the outside of the outer layer 7 and back inside the tampon again. As the removal cord is pulled, the part of the cord running through the outer layer comes essentially under tension first, and thus gathers the tampon's outer layer and increases the tampon's diameter.

It is clear that although, by way of example, only a loop 8 formed by one continuous cord has been shown, other methods can also be employed. One cord, or the ends of two cords, can easily be attached to the core layer to form a fixed connection so that all, or most, of the pulling directed to the cord/cords 8 increases the tampon's and, especially, its outer layer's diameter. There can also be more than two cords, so that the gathering of the layer 7 occurs at more than one point around the core layer 6, ensuring a more even transformation of the shape. It is not critical how the cords run, but the critical issue is to get the tractive force of the cord or cords 8 directed to the outer layer 7 in a way which alters its diameter.

The figures show clearly the principle of the invention, the tampon's diameter is increased after the tampon has been inserted into the vagina, or other cavity. This can be clearly understood without drawings for the anatomical parts for which the invention can be used.

The invention can be adapted in many ways still within its basic principle. Thus, for example, the removal cord 2 was presented as encasing the molding cord 1, while the molding cord slides in the 'channel' formed by the removal cord. This is not necessary. The removal cord's purpose is to be attached to the tampon so firmly, that the tampon can be pulled out of the vagina by it. The molding cord 1 can be fitted within the tampon even without being combined with the removal cord. A sliding connection with minimal friction is good, but the traction force needed for the molding is so minimal, that the friction to which the cord is subjected within the tampon makes no essential difference to it.

More than one absorbent outer layer can also be used for the embodiments shown in FIGS. 3–5.

What is claimed is:

1. An internally moldable tampon, comprising at least one oblong, liquid absorbent mass or layer and a removal and/or molding cord characterized in that the molding cord, or the combined molding and removal cord is situated in the tampon so that by pulling it following insertion of the tampon, the tampon loses at least some of its length and increases its circumference.

2. A tampon in accordance with claim 1, characterized in that the molding cord (1) is situated inside the tampon, attached to the end of the tampon which is furthest from the entrance to the vagina/cavity, facilitating the reduction of the lengthwise measurement of the tampon by pulling the cord (1).

3. A tampon in accordance with claim 1, characterized in that it consists of the core layer (6), with at least one outer layer (7) on top of it, and that pulling the cord (8) influences primarily the outer layer (7).

4. A tampon in accordance with claim 3, characterized in that it has only one combined molding and removal cord (8), which runs as a loop around the outer layer (7) and gathers it lengthwise together when the cord (8) is pulled.

5. A tampon in accordance with claim 4, characterized in that the combined molding and removal cord (8) runs as at least two loops around the outer layer (7).

\* \* \* \* \*